(12) United States Patent
Turner et al.

(10) Patent No.: US 6,596,019 B2
(45) Date of Patent: Jul. 22, 2003

(54) APPAREL VENTILATION SYSTEM

(75) Inventors: David Turner, Portland, OR (US); James C. Sell, Jr., Battle Ground, WA (US); Peter Belfanti, Portland, OR (US); Sheryll Sanchez, Gresham, OR (US)

(73) Assignee: Nike International Ltd., Beaverton, OR (US)

( * ) Notice: Subject to any disclaimer, the term of this patent is extended or adjusted under 35 U.S.C. 154(b) by 0 days.

(21) Appl. No.: 09/945,470

(22) Filed: Aug. 30, 2001

(65) Prior Publication Data

US 2003/0045918 A1 Mar. 6, 2003

(51) Int. Cl.[7] .................................................. A61F 7/00
(52) U.S. Cl. ....................................... 607/108; 607/107
(58) Field of Search ................................. 607/107, 108, 607/96, 104; 2/DIG. 1

(56) References Cited

U.S. PATENT DOCUMENTS

| | | | | |
|---|---|---|---|---|
| 4,572,188 A | * | 2/1986 | Augustine et al. | 607/107 |
| 4,738,119 A | | 4/1988 | Zafred | |
| 5,300,100 A | * | 4/1994 | Hickle et al. | 607/107 |
| 5,300,102 A | * | 4/1994 | Augustine et al. | 607/107 |
| 5,640,728 A | * | 6/1997 | Graebe | 5/606 |
| 5,658,325 A | * | 8/1997 | Augustine | 607/107 |
| 5,860,292 A | * | 1/1999 | Augustine et al. | 607/107 |
| 5,970,519 A | | 10/1999 | Weber | |
| 5,989,285 A | * | 11/1999 | DeVilbiss et al. | 607/107 |
| 6,102,936 A | * | 8/2000 | Augustine et al. | 607/96 |
| 6,245,096 B1 | * | 6/2001 | Tomic-Edgar et al. | 607/107 |
| 6,254,613 B1 | * | 7/2001 | Harrison | 607/108 |
| 6,371,976 B1 | * | 4/2002 | Vrzalik et al. | 607/104 |

FOREIGN PATENT DOCUMENTS

JP      11-323623      11/1999

* cited by examiner

*Primary Examiner*—Linda C. M. Dvorak
*Assistant Examiner*—Jocelyn Ram
(74) *Attorney, Agent, or Firm*—Banner & Witcoff, Ltd.

(57) ABSTRACT

A pressurized ventilation system for providing air to the body of an individual wearing the ventilation system to regulate the individual's body temperature is provided. The ventilation system includes the use of an air bladder defining an enclosed volume wherein there is located a plurality of channels for permitting airflow throughout the air bladder. The channels include a plurality of spaced apart apertures, which permit the escape of air out of the air bladder to the body of the individual wearing the ventilation system.

22 Claims, 3 Drawing Sheets

APPAREL VENTILATION SYSTEM

FIELD OF THE INVENTION

The present invention relates generally to apparel ventilation systems, and more particularly, to air bladder systems that may be incorporated with any apparel, accessory, or protective equipment to provide pressurized airflow to moderate the temperature of an individual.

BACKGROUND

Many professionals work in conditions where the usage of apparel and equipment prevent relief from extreme temperatures. For example, fire fighters and racecar drivers have to wear protective clothing that is heavy and impervious to moisture and gases. Many athletes wear heavy equipment, such as football or hockey protective gear. Such heavy equipment or protective clothing can lead to a person's body overheating.

In order to prevent overheating, ventilation systems have been developed that attempt to provide air flow to cool an individual in this type of situation. However these known systems have prohibitive drawbacks. For example, U.S. Pat. No. 4,738,119 to Zafred discloses a system, which uses high-pressure, porous tubes placed throughout insulating layers in a garment. Liquid carbon dioxide is added to the tubes, which is released in gaseous form to cool the wearer of the garment. However, the bulky tubing throughout the garment can be rigid and cause inflexibility of the garment and also discomfort for the wearer. For example, this type of tubing could injure a football player who is constantly hit and thrown to the ground. Because the tubes can be rigid and inflexible, there exists the possibility that the tubes will deteriorate and need to be replaced more often than a non-rigid type of device. In addition, the tubing and insulating layers surrounding the tubing add bulk to the cooling device creating heavier clothing and increasing the amount of cooling to be done. Further, the system does not always fit into the apparel or equipment for which the system may be required. The cooling system disclosed in Zafred also includes numerous parts, which require assembly, therefore, making it more expensive to manufacture.

Another known system is disclosed in U.S. Pat. No. 5,970,519 to Weber. The Weber patent discloses a two-layered garment for the medical profession with an outer layer being impermeable to air and an inner layer being air permeable. Air flows between the layers and reaches the body of the wearer through the inner, permeable layer. A disadvantage of this type of system is that there is no directed air flow. Additionally, if too much air is supplied to the garment, the amount of air holes throughout the garment may cause the garment to inflate, causing discomfort or inflexibility to the wearer. Also, due to the number of holes in the garment, a very large amount of air may be needed for the wearer to feel any type of cooling sensation.

Consequently, there exists a need for an apparel ventilation system that overcomes the disadvantages of the prior art.

BRIEF SUMMARY OF THE INVENTION

The present invention overcomes the disadvantages of the prior art by providing a ventilation system that delivers conditioned pressurized airflow for the regulation and/or moderation of temperature of the human body. The present invention provides a ventilation system that is not thick and bulky and can, therefore, lie flat when it is not in use. The present invention also provides a ventilation system that is comfortable to the user and has good air flow characteristics. The present invention further provides a ventilation system that has fewer parts and solid fittings, a simpler assembly and is, therefore, less expensive to manufacture.

Briefly, the present invention is directed to a pressurized ventilation system for providing air to a body of an individual wearing the ventilation system to regulate the temperature of the body. The ventilation system may comprise an air bladder defining an enclosed volume formed by a first wall and a second wall, the air bladder having a plurality of channels located between the first and second walls for permitting air flow throughout the air bladder, the channels include a plurality of apertures which extend through the first wall for permitting the escape of air out of the air bladder through the first wall. The ventilation system also includes a device for providing pressurized air to the air bladder.

BRIEF DESCRIPTION OF THE DRAWINGS

The invention will be better understood from consideration of the following description and the accompanying drawings. In the drawings, the following figures have the following general nature.

DETAILED DESCRIPTION

Figure 1:
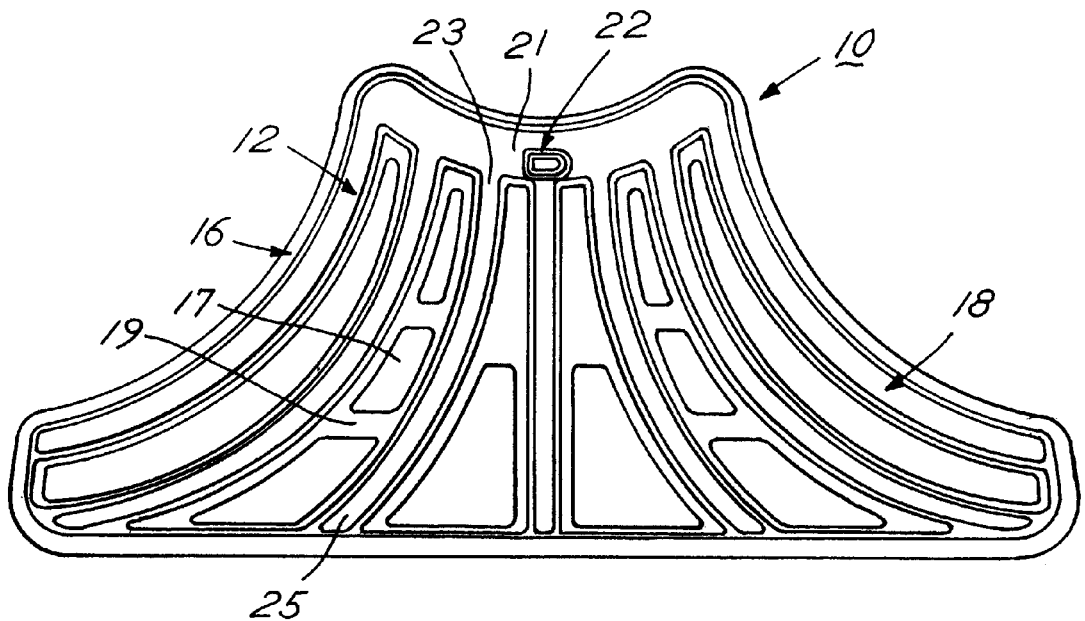
FIG. 1 is a front view of an embodiment of the present invention.
Figure 2:
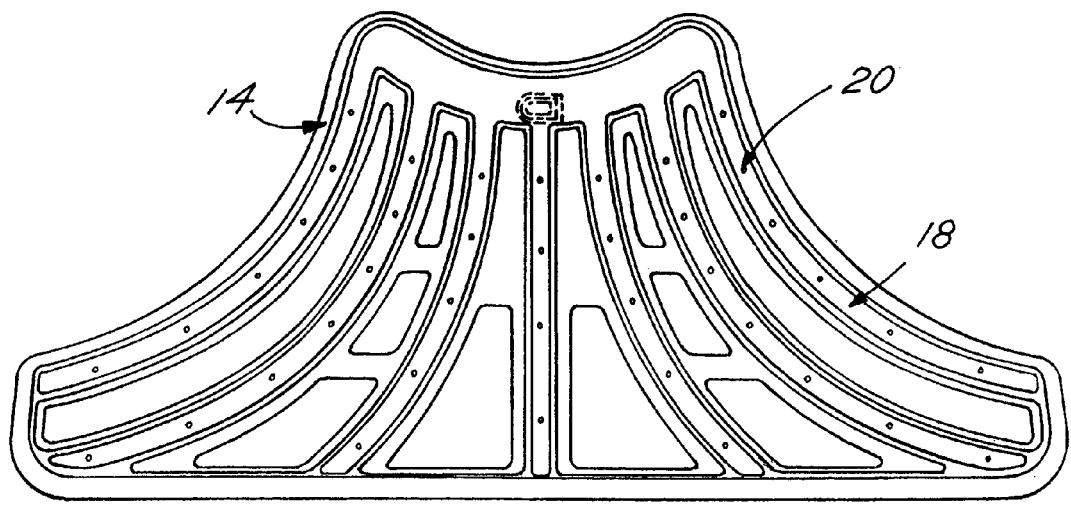
FIG. 2 is a rear view of invention in FIG. 1.

Referring to the drawings, there is shown in FIGS. 1 and 2 an exemplary embodiment of a ventilation system 10 of the present invention. The ventilation system 10 may be incorporated with, or attached to, any apparel, accessory or protective equipment, including, by way of example and not limitation, shirts, pants, jackets, hats, protective sports equipment, helmets, headgear, body suits, shoes, boots, gloves, pouches, capes, blankets, cushions, or any item used by an individual to which the regulation or moderation of the temperature of the body is desired. The ventilation system 10 may be used to accelerate the body's natural ability to cool itself with perspiration by using convection or evaporation to wick away perspiration from the wearer of the system. It should be understood that the ventilation system 10 may also be used to warm the body.

As depicted, the ventilation system 10 includes an air bladder 12, which is operatively connected to a source of air flow, for example, an air compressor, which may provide warm or cool air. It will be understood by those skilled in the art that other sources of airflow may be used with the present invention. The air bladder 12 may include an inner wall 14 and an outer wall 16. The inner and outer walls 14, 16 may be placed on top of one another and welded together, preferably using radio frequency (RF) welding, to form and define a volume having a network of channels 18 within the air bladder. While thermoplastic polyurethane (TPU) is preferred to form the inner and outer walls 14, 16 of the air bladder 12, any thermoplastic or similar material that is RF weldable and impermeable to air could be used with the present invention. With the use of TPU or a similar material to form the walls, the resulting air bladder 12 is flexible and flat making the device comfortable for the wearer. In an exemplary embodiment, the thickness of each wall is about 0.018 inches. However, the thickness may vary depending on the strength of the material and the air pressure used. Preferably, each wall has a thickness within the range of about 0.018 to 0.050 inches thick.

The channels 18 permit the air provided by the air source to flow throughout the air bladder 12. As preferred, the channels are operatively joined at a central location 21 so that a single source of airflow may be used with the ventilation system to effectively warm or cool the individual. Each channel defines an end open 23 and a closed end 25. The open end is operatively connected to the central location 21 and the closed end directs the airflow out through a plurality of apertures 22. In other words, airflow from a source of air is directed from the central location to the network of channels and out through a plurality of apertures 20 to cool or warm the body. In the exemplary embodiment shown in FIGS. 1–3, the configuration of the channels 18 is important to cool or warm the major muscle groups in the chest.

In one embodiment of the invention, the excess material between the channels is removed by a trim-out procedure. The removal of the excess material helps ventilate the wearer. When the excess material is removed, horizontal ribs 19 remain between the channels 18 which form at least one opening 17 between the channels 18 and the ribs 19. The horizontal ribs 19 help keep the channels from becoming twisted.

The inner wall 14, which faces the body of the wearer, contains the plurality of apertures 20 in the channels 18 through which air may escape from the air bladder 12 to reach the body of the wearer of the garment. The apertures 20 may be formed by any known manufacturing method, such as, by a hole punch. While the apertures 20 may be any size which would allow cooling or heating of the wearer of the ventilation system 10, tests have shown that to optimize the flow characteristics of the ventilation system 10, apertures of approximately 0.062 inches in diameter should be used.

As noted above, the air bladder 12 is operatively connected to a source of air flow. The outer wall 16 contains a fitting 22, which operatively connects the ventilation system 10 to an air source. It should be understood that the fitting 22 may be any valve or connection to a source of airflow that may be further used to regulate the flow of air from the air source. As depicted, the fitting 22 is a valve into which one end of a hollow barbed member may be inserted. The other end of the hollow barbed member may be inserted into tubing, which is connected directly to the air source.

To optimize the flow characteristics of the ventilation system 10, the fitting 22 should be placed in a location central to the channels 18. In the embodiment shown in FIG. 3, the fitting 22 is placed at the top of the air bladder 12 central to the channels 18 to allow easy access to hook up the air source and prevent interference with the wearer's equipment. In the embodiment shown in FIG. 4, the ventilation system may be used with a helmet or other headgear and the fitting might be placed at the bottom of the air bladder to allow for easy access to the air source without removing the helmet from the wearer's head. It should be apparent to those skilled in the art that the location of the fitting 22 depends on the type of garment or equipment with which the ventilation system is used. Optimally, the fitting should be placed so that it does not interfere with the wearer's apparel or other equipment.

Figure 3:
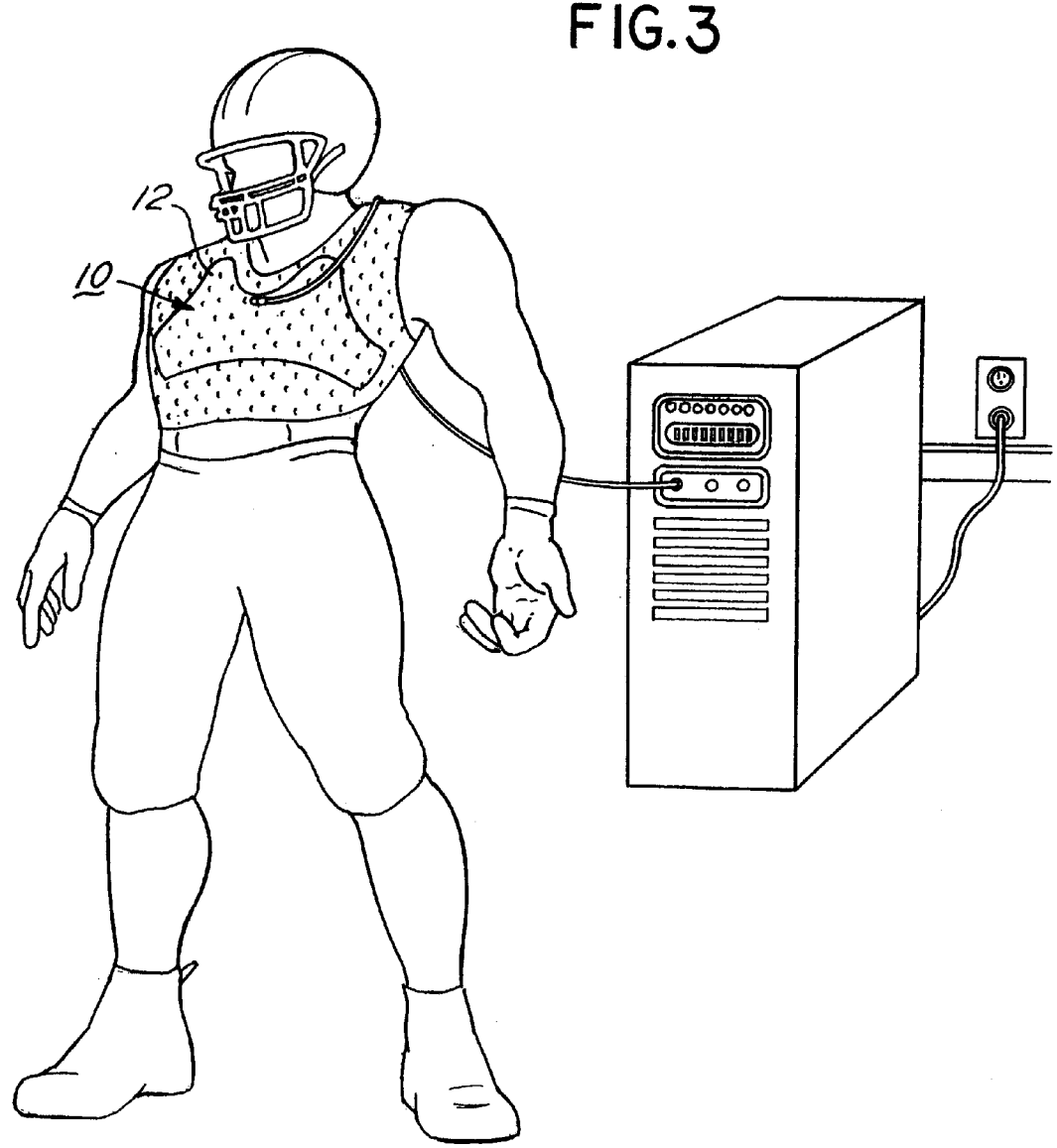
FIG. 3 shows an exemplary application of the invention of FIG. 1.
Figure 4:
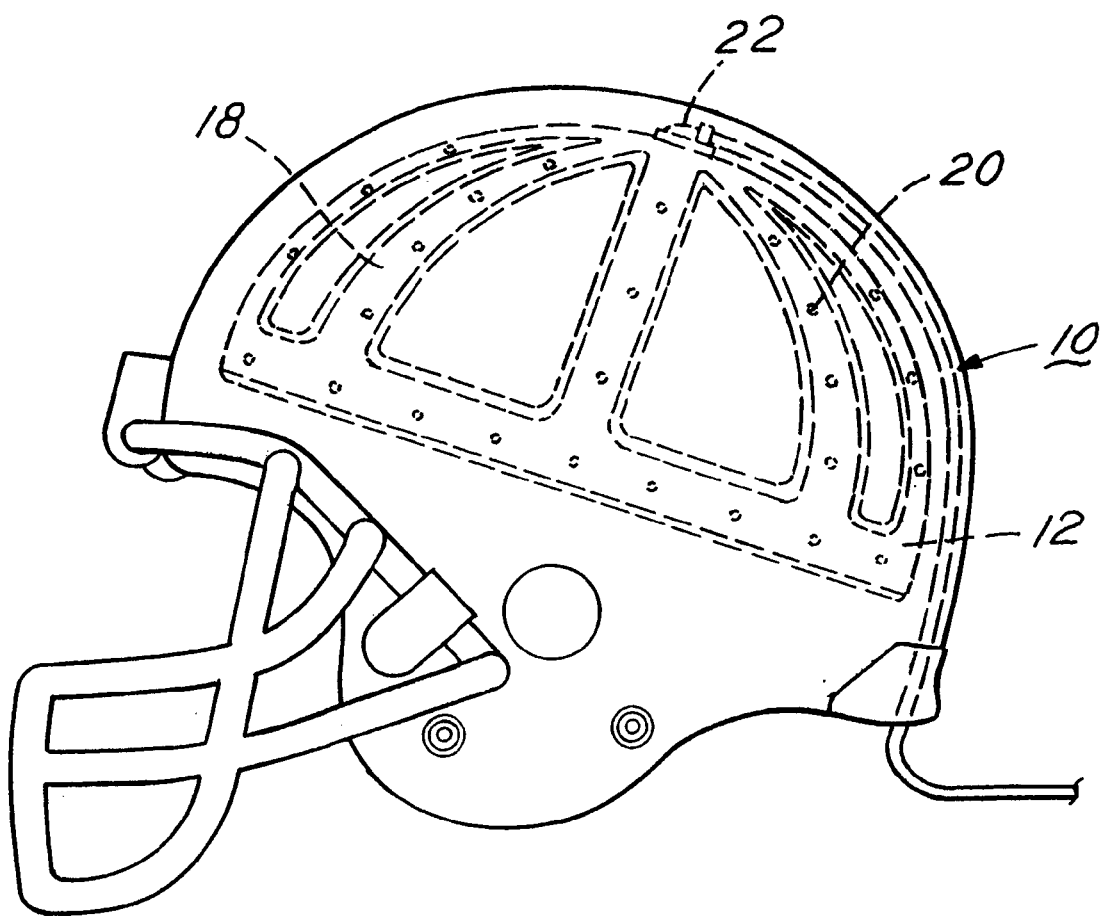
FIG. 4 shows another exemplary application of the invention.

Although the present invention could be used with a number of different types of air sources, FIG. 3 depicts a standard air compressor that has been shown to achieve the objectives of the present invention. The present invention is designed to work with straight compressed air with pressure in the range of 40 to 100 PSI (pounds per square inch), ideally using around 90 PSI. It will be understood that other fluids may be used with the invention, including dehumidified air to provide the desired cooling or heating effect.

The ventilation system 10 can be attached to a garment or equipment in a variety of ways known in the art. For example, the ventilation system 10 could be attached using hooks and loops, buttons or snaps. The ventilation system 10 could also be sewn into the garment or equipment. Those skilled in the art will recognize that other methods of attaching the ventilation system 10 to a garment or piece of equipment may be used.

It will be recognized that the illustrated embodiments can be modified in arrangement and detail without departing from the scope of the present invention. For example, in the case of firefighters or racecar drivers, a fireproofing process or material with a high melting point could be used with the invention. Therefore, to particularly point out and distinctly claim the subject matter regarded as the invention, the following claims conclude the specification.

What is claimed is:

1. A pressurized ventilation system for providing air to regulate the temperature of the body of an individual wearing the ventilation system, comprising:

an air bladder defining an enclosed volume formed by a first wall and a second wall, the air bladder having a plurality of channels located between the first and second walls for permitting air flow throughout the air bladder, at least one opening extending between the channels and through the first and second walls, the channels include a plurality of apertures which extend through the first wall for permitting the escape of air out of the air bladder through the first wall, and a source of airflow for providing pressurized air to the air bladder.

2. The pressurized ventilation system of claim 1 further comprising a fitting, joined to the air bladder, for operatively connecting the source of airflow to the air bladder.

3. The pressurized ventilation system of claim 2 wherein the plurality of channels are operatively joined at a central location.

4. The pressurized ventilation system of claim 3 wherein the fitting is located at the central location.

5. The pressurized ventilation system of claim 1 wherein the channels define an open end and a closed end, the open end permitting air flow into the channels, the closed end directing the air flow out of the apertures.

6. The pressurized ventilation system of claim 5 wherein the air bladder is made from a non-permeable material.

7. The pressurized ventilation system of claim 6 wherein the non-permeable material is thermoplastic urethane.

8. The pressurized ventilation system of claim 1 wherein the source of airflow is an air compressor.

9. The pressurized ventilation system of claim 1 wherein the plurality of channels are spaced apart along the air bladder.

10. The pressurized ventilation system of claim 9 further comprising at least one rib located between and connecting the spaced apart channels.

11. The pressurized ventilation system of claim 1 wherein the at least one opening is a plurality of openings.

12. The pressurized ventilation system of claim 1 wherein the air bladder is flexible and flat.

13. The pressurized ventilation system of claim 1 wherein the ventilation system is incorporated with an item selected from the group consisting of: shirts, pants, jackets, hats, protective sports equipment, helmets, headgear, body suits, shoes, boots, gloves, pouches, capes, blankets, and cushions.

14. A pressurized ventilation system for providing air to a body of an individual wearing the ventilation system to regulate the temperature of the body comprising:

a network of channels defining an enclosed volume formed by a first wall and a second wall, the first wall being in contact with the second wall to form the network of channels, the second wall includes a plurality of holes to allow air to exit the network of channels, at least one opening extending between the channels and through the first and second walls, and a fitting operatively connected to the network of channels for accepting pressurized air into the network of channels.

15. The pressurized ventilation system of claim 14 wherein the ventilation system is attached to a garment.

16. The pressurized ventilation system of claim 14 wherein the ventilation system is attached to protective equipment.

17. The pressurized ventilation system of claim 14 wherein the first and second walls are made from a non-permeable material.

18. A pressurized ventilation system for providing air to a body of an individual wearing the ventilation system to regulate the temperature of the body comprising:

a network of channels defining an enclosed volume formed by a first wall and a second wall, the first wall being in contact with the second wall to form the network of channels, each of the channels define a first end and a second end, the first ends of the channels being operatively joined, the second wall includes a plurality of holes to allow air to exit the network of channels, at least one opening extending between the channels and through the first and second walls.

19. The pressurized ventilation system of claim 18 further comprising a fitting operatively connected to the network of channels for accepting pressurized air into the network of channels.

20. The pressurized ventilation system of claim 19 wherein the ventilation system is incorporated with an item selected from the group consisting of: shirts, pants, jackets, hats, protective sports equipment, helmets, headgear, body suits, shoes, boots, gloves, pouches, capes, blankets, and cushions.

21. The pressurized ventilation system of claim 20 wherein the first and second walls are made from a non-permeable material.

22. The pressurized ventilation system of claim 21 wherein the non-permeable material is thermoplastic urethane.

* * * * *